United States Patent
Bánhegyi et al.

(10) Patent No.: US 8,802,849 B2
(45) Date of Patent: Aug. 12, 2014

(54) TRICYCLIC BENZO[4,5]THIENO-[2,3-D]PYRIMIDINE-4-YL-AMIN DERIVATIVES, THEIR SALTS, PROCESS FOR PRODUCING THE COMPOUNDS AND THEIR PHARMACEUTICAL USE

(75) Inventors: Péter Bánhegyi, Budapest (HU); György Kéri, Budapest (HU); László Örfi, Budapest (HU); Zsolt Székelyhidi, Budapest (HU); Frigyes Wáczek, Budapest (HU)

(73) Assignee: Vichem Chemie Kutató Kft., Budapest (HU)

( * ) Notice: Subject to any disclaimer, the term of this patent is extended or adjusted under 35 U.S.C. 154(b) by 798 days.

(21) Appl. No.: 12/918,136

(22) PCT Filed: Feb. 19, 2008

(86) PCT No.: PCT/HU2008/000016
§ 371 (c)(1),
(2), (4) Date: Oct. 4, 2010

(87) PCT Pub. No.: WO2009/104026
PCT Pub. Date: Aug. 27, 2009

(65) Prior Publication Data
US 2011/0015214 A1    Jan. 20, 2011

(51) Int. Cl.
*A61K 31/519* (2006.01)
*C07D 495/04* (2006.01)

(52) U.S. Cl.
CPC ............ *C07D 495/04* (2013.01); *A61K 31/519* (2013.01)
USPC ......................................... 544/250; 514/267

(58) Field of Classification Search
CPC ..................................................... C07D 495/04
USPC .......................................... 514/267; 544/250
See application file for complete search history.

(56) References Cited

FOREIGN PATENT DOCUMENTS

| | | | |
|---|---|---|---|
| DE | 237 663 | A1 | 7/1986 |
| DE | 245 666 | A1 | 5/1987 |
| DE | 245 667 | A1 | 5/1987 |
| JP | 2007-084494 | A | 4/2007 |
| WO | 97/13760 | A1 | 4/1997 |
| WO | 02/088138 | A1 | 11/2002 |
| WO | WO 02/088138 | * | 11/2002 ........... C07D 495/04 |
| WO | 03/057149 | A2 | 7/2003 |
| WO | 2004/032716 | A2 | 4/2004 |
| WO | 2006/044524 | A1 | 4/2006 |
| WO | 2006/136402 | A1 | 12/2006 |
| WO | 2007/059905 | A2 | 5/2007 |

OTHER PUBLICATIONS

El-Baih, et al., Synthesis of some thienopyrimidine derivatives, Molecules, 11(7), 498-513 (2006).*
Phoujdar, et al., Microwave-based synthesis of novel thienopyrimidine bioisosteres of gefitinib, Tetrahedron Letters 49, 1269-1273 (2008).*
Dave et al.; Reaction of Nitriles under Acidic Conditions. Part I. A General Method of Synthesis of Condensed Pyrimidines; Journal of Heterocyclic Chemistry; Nov. 1980; vol. 17, pp. 1497-1500.
Bhuiyan et al.; Screening of Fused Pyrimidines as Antimicrobial Agents: Inhibitory Activities of Some Tetrahydrobenzothieno-Pyrimidines; Pakistan Journal of Scientific and Industrial Research; 2005; vol. 48, No. 1, pp. 37-38.
Eissa et al., Synthesis and Antimicrobial Activity of Novel Tetrahydrobenzothienopyrimidines; Archives of Pharmacal Research; 2004; vol. 27, No. 9, pp. 885-892.
Ram et al.; Thieno[2,3-d]pyrimidines as Potential Chemotherapeutic Agents. II.; Journal of Heterocyclic Chemistry; 1981; vol. 18, No. 7, pp. 1277-1280.

* cited by examiner

*Primary Examiner* — Erich A Leeser
(74) *Attorney, Agent, or Firm* — Jason D. Voight

(57) ABSTRACT

The invention relates to novel tricyclic benzo[4,5]thieno-[2,3-d]pyrimidine-4-yl-amin derivatives, as well as their pharmaceutically acceptable salts. The subject of the invention too the process for producing the compounds and their use as a pharmaceutically active agent and as pharmaceutical compositions for prophylaxis and/or treatment of proliferative diseases such as cancer.

5 Claims, No Drawings

TRICYCLIC BENZO[4,5]THIENO-[2,3-D]PYRIMIDINE-4-YL-AMIN DERIVATIVES, THEIR SALTS, PROCESS FOR PRODUCING THE COMPOUNDS AND THEIR PHARMACEUTICAL USE

This is the National Phase of PCT/HU2008/000016, filed Feb. 19, 2008.

The present invention relates to novel tricyclic benzo[4,5]thieno-[2,3-d]pyrimidine-4-yl-amin derivatives (I), their pharmaceutically acceptable salts, to the process for producing the compounds and their use as a pharmaceutically active agent and as pharmaceutical compositions for prophylaxis and/or treatment of proliferative diseases such as cancer.

The novel compound have formula (I)

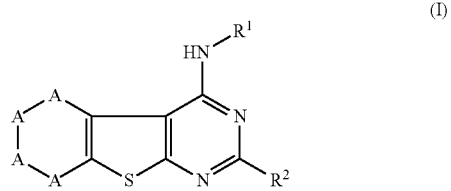

(I)

wherein:
A: methylene ($CH_2$), or methylidene (CH),
$R^1$: hydrogen, phenyl, mono-, di-, tri-, tetra-, or pentasubstitued phenyl, five or six membered ring with one or more heteroatom, saturated or unsaturated heterocycle, for example pyrazole, imidazole, isoxazole, furane, pyrrole, tiophene, thiasole, isothiazole, tiasole, pirane, piridine, pirimidine, dioxane, morpholine, thiomorpholine, pyridazine, pyrazine, piperazine,
$R^2$: hydrogen, substituted or unsubstituted alkyl or cycloalkyl.

The epidermal growth factor receptor protein tyrosine kinase (EGFR-PTK) is the archetypal member of a receptor tyrosine kinase family comprised of four closely related proteins called EGFR, HER2 (human EGF-related receptor), HER3 and HER4) All of these transmembrane receptors contain an intrinsic kinase activity that modifies tyrosine residues on the receptor itself as well as on downstream signaling molecules. This kinase activity is stimulated when members of the EGF family of growth factors bind to the receptor. EGFR signal transduction occurs via a multi-stage process initiated in normal cells by interactions between the receptor and ligand. Ligand binding to the extracellular domain induces receptors to dimerize. Dimerization can occur between two molecules of the same receptor (homodimerization) or between different members of EGFR family (heterodimerization) and activates the intracellular protein kinase domains of each receptor to cross-phosphorylate tyrosine residues of the other EGFR molecule. Preclinical studies have demonstrated a strong correlation between elevated levels of EGFR expression and tumorigenesis. In some cases, alterations in EGFR levels alone are sufficient to induce cancer. For example, cultured cells transfected with appropriate vectors acquire transformed behavior in culture when EGFR is overexpressed. Additionally, elevated levels of EGFRs have been detected in many different types of cultured human tumor cell lines including squamous-cell carcinoma (SCC) of the skin, oral cavity, esophagus and lung. There is evidence to suggest that similar alterations in EGFR expression may occur during human tumorigenesis or tumor progression as increased EGFR expression is frequently observed in breast, bladder, cervical, kidney, ovarian, lung and various SCCs.

Frequency of elevated EGFR expression in different types of epithelial tumors:

| Tumor type | Percentage of tumors expressing EGFR | Reference(s) |
|---|---|---|
| Head and neck | 80-100 | Salomon et al, Crit. Rev. Oncol. Hematol., 1995, 19, 183-232<br>Grandis et al, Cancer, 1996, 78, 1284-1292 |
| Renal cell | 50-90 | Salomon et al, Crit. Rev. Oncol. Hematol., 1995, 19, 183-232<br>Yoshida et al, Oncology, 1997, 54, 220-225 |
| Non-small-cell lung | 40-80 | Salomon et al, Crit. Rev. Oncol. Hematol., 1995, 19, 183-232<br>Rusch et al, Clin Cancer Res., 1997, 37, 515-522<br>Fontanini et al, Clin. Cancer Res., 1998, 4, 241-249<br>Fujino et al, Eur. J. Cancer, 1996, 32, 2070-2074<br>Franklin WA, Veve R, Hirsch FR, Helfrich BA, Semin Oncol. 2002, 29, 3-14 |
| Glioma | 40-50 | Salomon et al, Crit. Rev. Oncol. Hematol., 1995, 19, 183-232<br>Rieske et al, Pol. J. Pathol, 1998, 49, 145-149 |
| Ovarian | 35-70 | Salomon et al, Crit. Rev. Oncol. Hematol., 1995, 19, 183-232<br>Bartlett et al, Br. J. Cancer, 1996, 73, 301-306 |
| Bladder | 31-48 | Salomon et al, Crit. Rev. Oncol. Hematol., 1995, 19, 183-232<br>Chow et al, Anticancer Res., 1997, 17, 1293-1296 |
| Pancreatic | 30-50 | Salomon et al, Crit. Rev. Oncol. Hematol., 1995, 19, 183-232<br>Uegaki et al, Anticancer Res., 1997, 17, 3841-3847 |
| Colon | 25-77 | Salomon et al, Crit. Rev. Oncol. Hematol., 1995, 19, 183-232<br>Messa et al, Acta Oncol, 1998, 37, 285-289 |
| Breast | 14-91 | Klijn et al, Endocr. Rev., 1992, 13, 3-17<br>Walker and Dearing, Breast Cancer Res. Treat., 1999, 53, 167-176<br>Beckman et al, Oncology, 1996, 53, 441-447 |
| Prostate | N/A | Barton J, Blackledge G, Wakeling A Urology. 2001, 58, 114-122 |

Inhibitors of the EGFR-PTK are therefore accepted to have great therapeutic potential in the treatment of malignant and nonmalignant epithelial diseases (many type of cancer), and proliferative disorders of the epidermis such as psoriasis. [1,2,3] Due to the involvement of tyrosine kinases in many signal transduction pathways, it will be important to develop inhibitors with high selectivity at the enzyme level.

In recent years, a number of different classes of compounds have been reported as tyrosine kinase inhibitors and reviewed in several articles [4-7].

1. Aaronson, S. A. Growth Factors and Cancer. Science, 1991, 254, 1146-1152
2. Ullrich, A.; Schlessinger, J. Signal Transduction by Receptors with Tyrosine Kianse Activity Cell, 1990, 61, 203-212
3. Elder. J. T.; Fischer, G. J.; Lindquist, P. B.; Bennett, G. L.; Pittelkow, M. R.; Coffey. R. J.; Ellingsworth, L.; Derynck, R.; Voorhees, J. J. Overexpression of transforming growth factor α in psoriatic epidermis. Science, 1989, 243, 811-814
4. Burke. T. R. Protein-Tyrosine Kinase Inhibitors, Drugs Future, 1992, 17, 119-131
5. Fry, D. W. Protein tyrosine kinases as therapeutic targets in cancer chemotherapy and recent advances in the development of new inhibitors. Exp Opin. Invest. Drugs, 1994, 3 (6), 577-595

6. Levitzki, A.; Gazit, A. Tyrosine Kinase Inhibition: An Approach to Drug Development. Science, 1995, 267, 1782-1788
7. Ullrich A et al Nature, 1984 309, 418-425.

The present invention is relating to compounds of the formula (I):

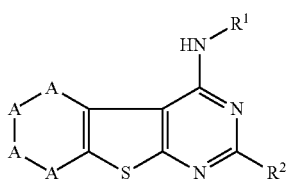

(I)

wherein:

A: methylene ($CH_2$), or methylidene (CH), $R^1$: hydrogen, phenyl, mono-, di-, tri-, tetra-, or pentasubstitued phenyl, five or six membered ring with one or more heteroatom, saturated or unsaturated heterocycle, for example pyrazole, imidazole, isoxazole, furane, pyrrole, tiophene, thiasole, isothiazole, tiasole, pirane, piridine, pirimidine, dioxane, morpholine, thiomorpholine, pyridazine, pyrazine, piperazine.

$R^2$: hydrogen, substituted or unsubstituted alkyl or cycloalkyl.

The following compounds are representative of the compounds of formula (I):

| Com | A | $R^1$ | $R^2$ | |
|---|---|---|---|---|
| 1 | $CH_2$ | 2-F—Ph | H | (2-Fluoro-phenyl)-(5,6,7,8-tetrahydro-benzo[4,5]thieno[2,3-d]pyrimidin-4-yl)-amine |
| 2 | $CH_2$ | 3-F—Ph | H | (3-Fluoro-phenyl)-(5,6,7,8-tetrahydro-benzo[4,5]thieno[2,3-d]pyrimidin-4-yl)-amine |
| 3 | $CH_2$ | 3-Br—Ph | H | (3-Bromo-phenyl)-(5,6,7,8-tetrahydro-benzo[4,5]thieno[2,3-d]pyrimidin-4-yl)-amine |
| 4 | $CH_2$ | 3-$NH_2$—Ph | H | N-(5,6,7,8-Tetrahydro-benzo[4,5]thieno[2,3-d]pyrimidin-4-yl)-benzene-1,3-diamine |
| 5 | $CH_2$ | 3-CN—Ph | H | 3-(5,6,7,8-Tetrahydro-benzo[4,5]2,3-d]pyrimidin-4-ylamino)-benzonitrile |
| 6 | $CH_2$ | 4-F—Ph | H | (4-Fluoro-phenyl)-(5,6,7,8-tetrahydro-benzo[4,5]thieno[2,3-d]pyrimidin-4-yl)-amine |
| 7 | $CH_2$ | 4-Cl—Ph | H | (4-Chloro-phenyl)-(5,6,7,8-tetrahydro-benzo[4,5]thieno[2,3-d]pyrimidin-4-yl)-amine |
| 8 | $CH_2$ | 4-$NH_2$—Ph | H | N-(5,6,7,8-Tetrahydro-benzo[4,5]thieno[2,3-d]pyrimidin-4-yl)-benzene-1,4-diamine |
| 9 | $CH_2$ | 3-Cl—Ph | cPr | (3-Chloro-phenyl)-(2-cyclopropyl-5,6,7,8-tetrahydro-benzo[4,5]thieno[2,3-d]pyrimidin-4-yl)-amine |
| 10 | $CH_2$ | 3-OH—Ph | cPr | 3-(2-Cyclopropyl-5,6,7,8-tetrahydro-benzo[4,5]thieno[2,3-d]pyrimidin-4-ylamino)-Phenol |
| 11 | $CH_2$ | 3-$CF_3$—Ph | cPr | (2-Cyclopropyl-5,6,7,8-tetrahydro-benzo[4,5]thieno[2,3-d]pyrimidin-4-yl)-(3-trifluoromethyl-phenyl)-amine |
| 12 | $CH_2$ | 3-$NH_2$—Ph | cPr | N-(2-Cyclopropyl-5,6,7,8-tetrahydro-benzo[4,5]thieno[2,3-d]pyrimidin-4-yl)-benzene-1,3-diamine |
| 13 | $CH_2$ | 3-$NO_2$—Ph | cPr | (2-Cyclopropyl-5,6,7,8-tetrahydro-benzo[4,5]thieno[2,3-d]pyrimidin-4-yl)-(3-nitro-phenyl)-amine |
| 14 | $CH_2$ | 3-CN—Ph | cPr | 3-(2-Cyclopropyl-5,6,7,8-tetrahydro-benzo[4,5]thieno[2,3-d]pyrimidin-4-ylamino)-benzonitrile |
| 15 | $CH_2$ | 3-OMe—Ph | cPr | (2-Cyclopropyl-5,6,7,8-tetrahydro-benzo[4,5]thieno[2,3-d]pyriminidin-4-yl)-(3-methoxy-phenyl)-amine |
| 16 | CH | 3-F—Ph | cPr | (2-Cyclopropyl-benzo[4,5]thieno[2,3-d]pyrimidin-4-yl)-(3-fluoro-phenyl)-amine |
| 17 | CH | 3-Cl—Ph | cPr | (2-Cyclopropyl-benzo[4,5]thieno[2,3-d]pyrimidin-4-yl)-(3-chloro-phenyl)-amine |
| 18 | CH | 3-Br—Ph | cPr | (2-Cyclopropyl-benzo[4,5]thieno[2,3-d]pyrimidin-4-yl)-(3-bromo-phenyl)-amine |
| 19 | CH | 3-OH—Ph | cPr | 3-(2-Cyclopropyl-benzo[4,5]thieno[2,3-d]pyrimidin-4-ylamino)-phenol |
| 20 | CH | 3-OMe—Ph | cPr | 3-(2-Cyclopropyl-benzo[4,5]thieno[2,3-d]pyrimidin-4-yl)-(3-methoxy-phenyl)-amine |
| 21 | CH | 3-F—Ph | H | Benzo[4,5]thieno[2,3-d]pyrimidin-4-yl-(3-fluoro-phenyl)-amine |

| Com | A | R¹ | R² | |
|---|---|---|---|---|
| 22 | CH | 3-Cl—Ph | H | Benzo[4,5]thieno[2,3-d]pyrimidin-4-yl-(3-chloro-phenyl)-amine |
| 23 | CH | 3-Br—Ph | H | Benzo[4,5]thieno[2,3-d]pyrimidin-4-yl-(3-bromo-phenyl)-amine |

The subject of the invention as well the use of compounds according to the above compounds or the compounds in form of pharmaceutical compositions for prophylaxis and/or treatment of proliferative diseases such as cancer.

The invention is relates to the process for producing compounds of the formula (I) and their pharmaceutically acceptable salts where R1, R2 and A are as mentioned above. According to the process cyclohexanone is condensed with cyan-acetic acid ethylester and elementary sulfur in equimolar proportions in watery and alcoholic solution under heating then the produced amine derivative of the formula (IV) is transformed to a thieno-pyrimidine compound of the formula (Va) by heating with formamide in a ring closing reaction; or the compound of formula (IV) is brought into reaction with R3-carbonyl chloride where R3 is substituted or unsubstituted alkyl or cyclopropyl group in presence of a base and transformed to an acyl derivative of formula (VI) where R3 is as mentioned above then the received compound is heated with aqua ammonia and the compound of closed ring of formula (Vb) where R3 is as mentioned above is produced in this way; or B.) cyclohexanone is condensed with cyan acetic acid ethylester and elementary sulfur in equimolar proportions in watery and alcoholic solution under heating then the produced amine derivative of formula (IV) is brought into reaction with R3 carbonyl chloride where R3 is substituted or unsubstituted alkyl or cyclopropyl group, in presence of a base and transformed to a compound of formula (VI) where R3 is as mentioned above then the compound produced in this way is refluxed in a medium containing organic solvent and in presence of manganese dioxide and the produced compound of formula (VII) where R3 is as mentioned above is mixed in aqua ammonia under heating and the compound of formula (VIII) is produced where R3 is as mentioned above;

or the compound of formula (VII) where R3 is as mentioned above is mixed in methane sulfonic acid at room temperature then the mixture is poured into icy aqua ammonia then the compound of formula (IX) produced in this way is mixed in formamide under heating producing the compound of formula (X);

then the compounds of formula (Va) or (Vb) named collectively (V) where R2 is as mentioned above or the compound of formula (VIII) where R3 is as mentioned above or the compound of formula (X) is heated in phosphorus oxychloride under mixing then the produced halogenized derivative is brought into reaction with an amine of formula R1-NH2 where R1 is as mentioned above in alcoholic medium under heating then the received compound is optionally transformed into salt then the product is isolated in a known way.

Analytical Methods.

HPLC-MS

LC-MS analyses were performed by Waters chromatograph/ZMD mass spectrometer equipped with Waters 996 DAD UV detector Waters 2700 autosampler and Waters 600 controller.

Supelco Discovery RP-AmideC16 column was used in gradient mode at 3 milliliter/min flow rate.

Initial solvent: 10% AcCN/90% Water/0.05% HCOOH. Solvent B: 100% AcCN

Gradient: 0% B till 30 sec, 0-80% between 30-120 sec, 80% till 240 sec, 80-0% between 240-260 sec, 0% till 360 sec.

Injection: 5 µg

Solvents were purchased from Riedel-deHaën Company (Acetonitrile G Chromasolv (34998)

Formic acid extra pure (27001) Distilled water was purified by Mili-Q Academic equipment.

Details of mass spectrometry: Ionization: ES+/ES−, Source block temp: 120° C.

Desolvation temp: 350° C. Desolvation Gas: 400 L/min Cone Gas: 100 L/min

Capillary: 3000 V Cone: 25 V

Extractor: 3 V Rf, Lens: 0.2 V, Scan: 120 to 1000 m/z in 1 sec, Inter-scan delay: 0.1 s

NMR

300 MHz H¹-NMR analyses were performed by Bruker AC-300 equipment at 25° C. DMSO-d₆ was generally used as solvent while the exceptions are given.

General Synthetic Methods:

A process of making a compound of the formula (I) below can be made by the following general scheme:

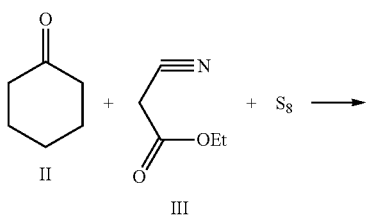

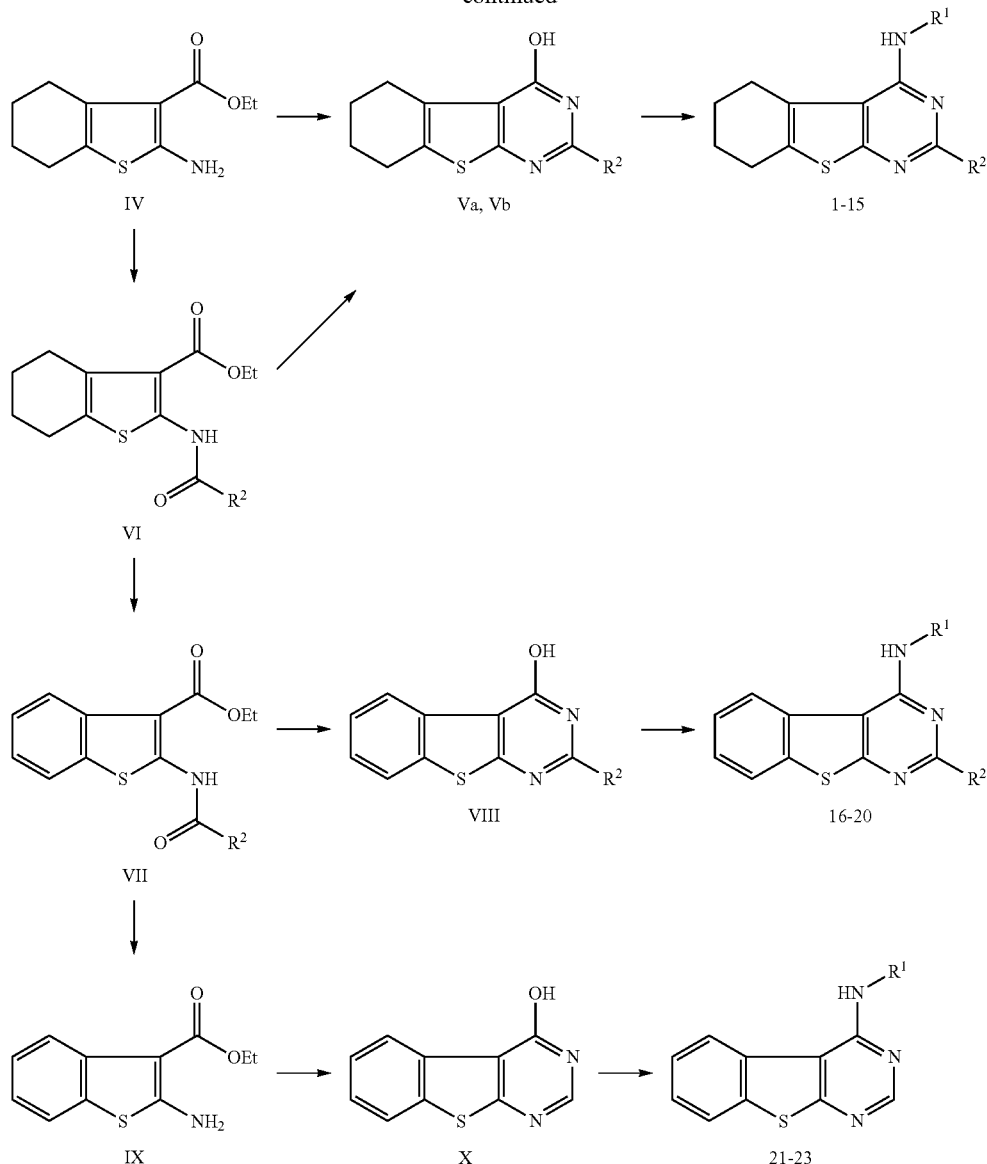

EXAMPLE 1

Preparation of 2-Amino-4,5,6,7-tetrahydro-benzo[b]thiophene-3-carboxylic acid ethyl ester (IV)

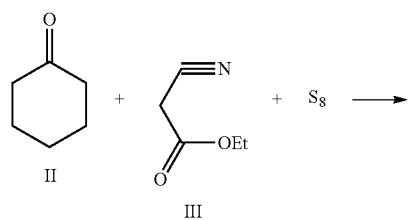

-continued

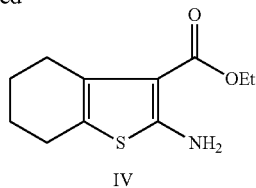

1 mol cyclohexanone and 1 mol cyano-acetic acid ethyl ester were solved in 800 milliliter ethyl alcohol, 1 mol sulphur and 35 milliliter distilled water were added to the solution. The mixture was cooled down between to 3-5° C. and 35 milliliter triethyl-amine was added to it. The reaction mixture was stirred for 2 hours at reflux temperature then it was allowed to cool down to room temperature. The precipitated solid was wiltered off, washed with water and n-hexane, then dried.

Yield: 77%.

Preparation of 5,6,7,8-Tetrahydro-benzo[4,5]thieno[2,3-d]pyrimidin-4-ol (Va)

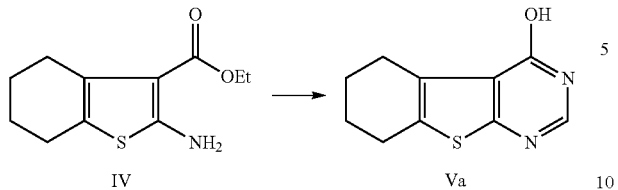

A solution of 10 millimol IV in 15 milliliter formamide was stirred at 100° C. for 3 hours then cooled down to room temperature. The reaction mixture was poured onto crushed ice with continuous stirring then collected by filtration. The product was washed with water and n-hexane, then dried.

Yield: 65%

Preparation of 2-Cyclopropyl-5,6,7,8-tetrahydro-benzo[4,5]thieno[2,3-d]pyrimidin-4-ol (Vb)

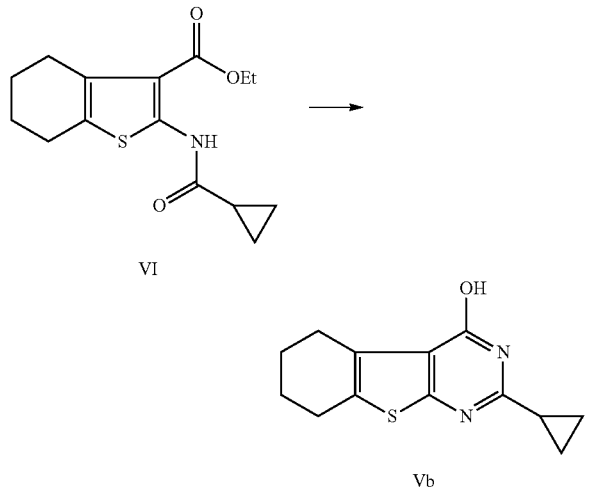

A suspension of 10 millimol IV in 10 milliliter 25% aqueous $NH_3$ was stirred at 90° C. for 24 hours in closed vial. The reaction mixture was cooled down to room temperature, and poured onto crushed ice with continuous stirring then collected by filtration. The product was washed with water and n-hexane, then dried.

Yield: 88%

EXAMPLE 2

Preparation of compounds 1-15

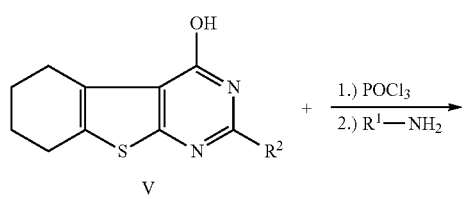

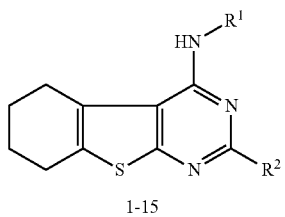

The solution of 1 millimol V in 5 mL $POCl_3$ was stirred at 100° C. for 3 hours. The reaction mixture was cooled down to room temperature, and poured onto crushed ice with continuous stirring. The solid was filtered off, washed with n-hexane and dried over $P_2O_5$. This product and 2 millimol amine reagent were solved in 2.5 milliliter propan-2-ol, and the solution was stirred at 100° C. for 6 hours in closed vial. The reaction mixture was poured onto crushed ice with continuous stirring, the pH was adjusted with 1N aqueous HCl to pH=7. The solid was filtered off, washed with water and n-hexane then dried.

Yields: 66-85° A

Compound 1-15 were prepared according to this method.

| Com | A | $R^1$ | $R^2$ | |
|---|---|---|---|---|
| 1 | $CH_2$ | 2-F—Ph | H | (2-Fluoro-phenyl)-(5,6,7,8-tetrahydro-benzo[4,5]thieno[2,3-d]pyrimidin-4-yl)-amine |
| 2 | $CH_2$ | 3-F—Ph | H | (3-Fluoro-phenyl)-(5,6,7,8-tetrahydro-benzo[4,5]thieno[2,3-d]pyrimidin-4-yl)-amine |
| 3 | $CH_2$ | 3-Br—Ph | H | (3-Bromo-phenyl)-(5,6,7,8-tetrahydro-benzo[4,5]thieno[2,3-d]pyrimidin-4-yl)-amine |
| 4 | $CH_2$ | 3-$NH_2$—Ph | H | N-(5,6,7,8-Tetrahydro-benzo[4,5]thieno[2,3-d]pyrimidin-4-yl)-benzene-1,3-diamine |
| 5 | $CH_2$ | 3-CN—Ph | H | 3-(5,6,7,8-Tetrahydro-benzo[4,5]thieno[2,3-d]pyrimidin-4-ylamino)-benzonitrile |
| 6 | $CH_2$ | 4-F—Ph | H | (4-Fluoro-phenyl)-(5,6,7,8-tetrahydro-benzo[4,5]thieno[2,3-d]pyrimidin-4-yl)-amine |
| 7 | $CH_2$ | 4-Cl—Ph | H | (4-Chloro-phenyl)-(5,6,7,8-tetrahydro-benzo[4,5]thieno[2,3-d]pyrimidin-4-yl)-amine |
| 8 | $CH_2$ | 4-$NH_2$—Ph | H | N-(5,6,7,8-Tetrahydro-benzo[4,5]thieno[2,3-d]pyrimidin-4-yl)-benzene-1,4-diamine |
| 9 | $CH_2$ | 3-Cl—Ph | cPr | (3-Chloro-phenyl)-(2-cyclopropyl-5,6,7,8-tetrahydro-benzo[4,5]thieno[2,3-d]pyrimidin-4-yl)-amine |
| 10 | $CH_2$ | 3-OH—Ph | cPr | 3-(2-Cyclopropyl-5,6,7,8-tetrahydro-benzo[4,5]thieno[2,3-d]pyrimidin-4-ylamino)-Phenol |
| 11 | $CH_2$ | 3-$CF_3$—Ph | cPr | (2-Cyclopropyl-5,6,7,8-tetrahydro-benzo[4,5]thieno[2,3-d]pyrimidin-4-yl)-(3-trifluoromethyl-phenyl)-amine |
| 12 | $CH_2$ | 3-$NH_2$—Ph | cPr | N-(2-Cyclopropyl-5,6,7,8-tetrahydro-benzo[4,5]thieno[2,3-d]pyrimidin-4yl)-benzene-1,3-diamine |
| 13 | $CH_2$ | 3-$NO_2$—Ph | cPr | (2-Cyclopropyl-5,6,7,8-tetrahydro-benzo[4,5]thieno[2,3-d]pyrimidin-4-yl)-(3-nitro-phenyl)-amine |
| 14 | $CH_2$ | 3-CN—Ph | cPr | 3-(2-Cyclopropyl-5,6,7,8-tetrahydro-benzo[4,5]thieno[2,3-d]pyrimidin-4-ylamino)-benzonitrile |
| 15 | $CH_2$ | 3-OMe—Ph | cPr | (2-Cyclopropyl-5,6,7,8-tetrahydro-benzo[4,5]thieno[2,3-d]pyrimidin-4-yl)-(3-methoxy-phenyl)-amine |

Physicochemical properties of compounds 1-15.

| Comp | MW [g/mol] | mp [°C.] | ¹H-NMR δ [ppm] in DMSO-$d_6$ |
|---|---|---|---|
| 1 | 299.37 | 160.7 | 1.83(bs, 4H, $CH_2$), 2.83(bs, 2H, $CH_2$), 3.16 (bs, 2H, $CH_2$), 7.25(bs, 2H, ArH), 7.80(bs, 1H, ArH), 8.20(s,1H, ArH), 8.35(s, 1H, ArH), 8.60(bs, 1H, NH) |
| 2 | 299.37 | 210.6 | 1.85(bs, 4H, $CH_2$), 2.84(bs, 2H, $CH_2$), 3.14 (bs, 2H,$CH_2$), 6.91(t, 1H, ArH, J = 8.22), 7.45(m, 2H, ArH), 7.66(d, 1H, ArH, J = 11.67), 8.39(s, 1H, ArH), 8.48(s, 1H, NH) |
| 3 | 360.28 | 169 | 1.85(bs, 4H, $CH_2$), 2.84(bs, 2H, $CH_2$), 3.13 (bs, 2H, $CH_2$), 7.28(m, 2H, ArH),7.70(d, 1H, ArH, J = 5.11), 7.97(s, 1H, ArH), 8.25(s, 1H, ArH), 8.44(s, 1H, NH) |
| 4 | 296.40 | 164.3 (d) | 1.84(bs, 4H, $CH_2$), 2.82(bs, 2H, $CH_2$), 3.11 (bs, 2H, $CH_2$), 6.30(d, 1H, ArH, J = 6.23), 6.93(m, 3H, ArH), 7.86(bs, 1H, ArH), 8.38 (s, 1H, NH) |
| 5 | 306.39 | 194.6 | 1.84(bs, 4H, $CH_2$), 2.83(bs, 2H, $CH_2$), 3.12 (bs, 2H, $CH_2$), 6.56(bs, 1H, ArH), 7.04(bs, 1H, ArH),7.16(bs, 1H, ArH), 7.99(bs, 1H, ArH), 8.26(bs, 1H, ArH), 8.43(s, 1H, NH) |
| 6 | 299.37 | 213 | 1.85(bs, 4H, $CH_2$), 2.83(bs, 2H, $CH_2$), 3.13(bs, 2H, $CH_2$), 7.21(t, 2H, ArH, J = 8.61), 7.62(d, 2H, ArH, J = 5.04), 8.40(bs, 2H, ArH, NH) |
| 7 | 315.83 | 191.2 | 1.85(bs, 4H, $CH_2$), 2.84(bs, 2H, $CH_2$), 3.13 (bs, 2H, $CH_2$), 7.41(d, 2H, ArH, J = 8.61), 7.68(d, 2H, ArH, J = 8.64), 8.40(s, 1H, ArH), 8.44(s, 1H, NH) |
| 8 | 296.40 | 203.1 | 1.83(bs, 4H, CH, ), 2.79(bs, 2H, $CH_2$), 3.08(bs, 2H, $CH_2$), 6.56(d, 2H, ArH, J = 8.01), 7.19 (d, 2H, ArH, J = 7.98), 7.77(s, 1H, ArH), 8.22(s, 1H, NH) |
| 9 | 355.89 | 208.6 | 1.03(m, 4H, $CH_2$), 1.84(bs, 4H, $CH_2$), 2.12(m, 1H, CH), 2.81(bs, 2H, $CH_2$), 3.10(bs, 2H, $CH_2$), 7.16(d, 1H, ArH, J = 7.92), 7.38(t, 1H, ArH, J = 8.04), 7.60(d, 2H, ArH, J = 8.16), 7.86(t, 1H, ArH, J = 1.89), 8.42(s, 1H, NH) |
| 10 | 337.45 | 239.7 | 1.05(m, 4H, $CH_2$), 1.83(bs, 4H, $CH_2$), 2.15(bs, 1H, CH), 2.81(bs, 2H, $CH_2$), 3.09(bs, 2H, $CH_2$), 6.57(d, 1H, ArH, J = 7.59), 7.11(m, 3H, ArH), 8.40(s, 1H, NH) |
| 11 | 389.45 | 204.8 | 1.00(m, 4H, $CH_2$), 1.85(bs, 4H, $CH_2$), 2.12(m, 1H, CH), 2.82(bs, 2H, $CH_2$), 3.12(bs, 2H, $CH_2$), 7.43(d, 1H, ArH, J = 7.68), 7.59(t, 1H, ArH, J = 7.92), 7.87(d, 1H, ArH, J = 8.13), 8.20 (s, 1H, ArH),, 8.53(s, 1H, NH) |
| 12 | 336.46 | 185.9 | 0.94(m, 4H, $CH_2$), 1.82(bs, 4H, $CH_2$), 2.04 (bs, 1H, CH), 2.76(bs, 2H, $CH_2$), 3.05(bs, 2H, $CH_2$), 5.03(s, 2H, $NH_2$), 6.28(d, 1H, ArH, J = 7.56), 6.96(m, 3H, ArH), 7.68(s, 1H, NH) |
| 13 | 366.44 | 211.7 | 1.00(bs, 4H, $CH_2$), 1.84(bs, 4H, $CH_2$), 2.11(m, 1H, CH), 2.81(bs, 2H, $CH_2$), 3.13(bs, 2H, $CH_2$), 7.62(t, 1H, ArH, J = 8.13), 7.92(d, 1H, ArH, J = 7.92), 8.02(d, 1H, ArH, J = 7.38), 8.62(s, 1H, ArH), 8.77(s, 1H, NH) |
| 14 | 346.46 | 176.3 | 1.00(m, 4H, $CH_2$), 1.84(bs, 4H, $CH_2$), 2.10(m, 1H, CH), 2.80(bs, 2H, $CH_2$), 3.10(bs, 2H, $CH_2$), 7.54(m, 2H, ArH), 7.98(m, 1H, ArH), 8.16(s, 1H, ArH), 8.44(s, 1H, NH) |
| 15 | 351.47 | 186.7 | 1.03(m, 4H, $CH_2$), 1.84(bs, 4H, $CH_2$), 2.13(m, 1H, CH), 2.81(bs, 2H, $CH_2$), 3.78(s, 3H, $CH_3$), 6.71(d1H, ArH, J = 5.94), 7.17(d, 1H, ArH, J = 8.10), 7.27(t, 1H, ArH, J = 8.13), 7.40(s, 1H, ArH), 8.35(s, 1H, NH) |

EXAMPLE 3

Preparation of 2-(Cyclopropanecarbonyl-amino)-4,5,6,7-tetrahydro-benzo[b]thiophene-3-carboxylic acid ethyl ester (VI)

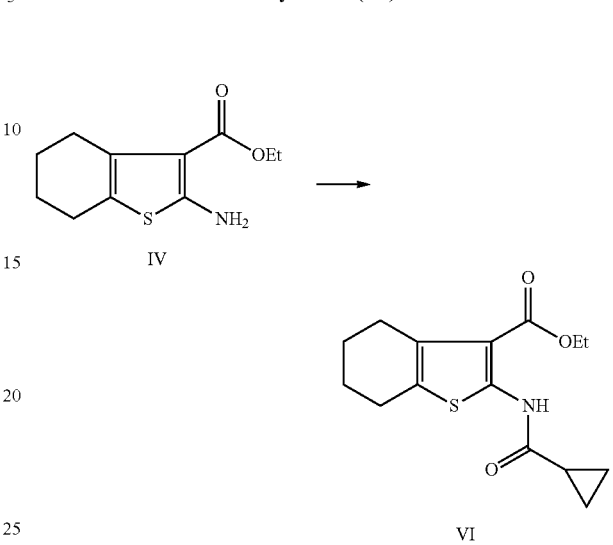

11 millimol cyclopropanecarbonyl chloride was added dropwise to the solution of 10 millimol IV in 25 milliliter pyridine at 5° C. The reaction mixture was stirred at this temperature for 1 hour, poured onto icecold 1N aqueous HCl, the precipitated solid was filtered off, washed with water and n-hexane, then dried.
Yield: 80%

Preparation of 2-(Cyclopropanecarbonyl-amino)-benzo[b]thiophene-3-carboxylic acid ethyl ester (VII)

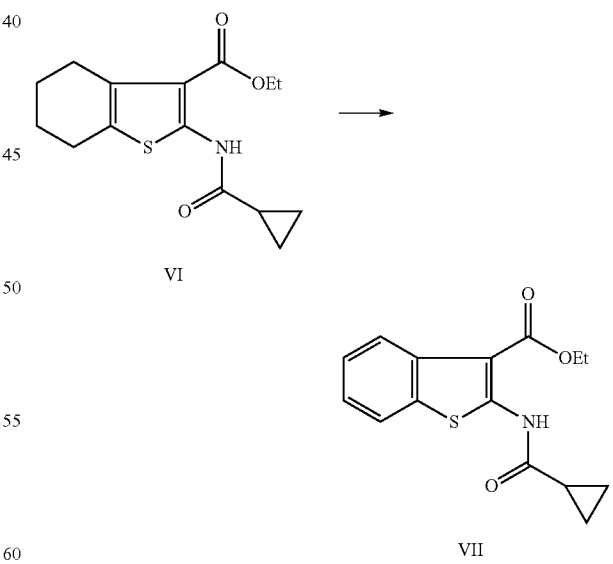

8.00 g $MnO_2$ (Activated, Fluka) was added to the suspension of 10 millimol VI in 60 milliliter toluene, and the suspension was stirred at reflux temperature for 5 days. The reaction mixture cooled down to 60° C., filtrated, and evaporated to give the desired compound VII as solid crystal.
Yield: 72%

Preparation of 2-Cyclopropyl-benzo[4,5]thieno[2,3-d]pyrimidin-4-ol (VIII)

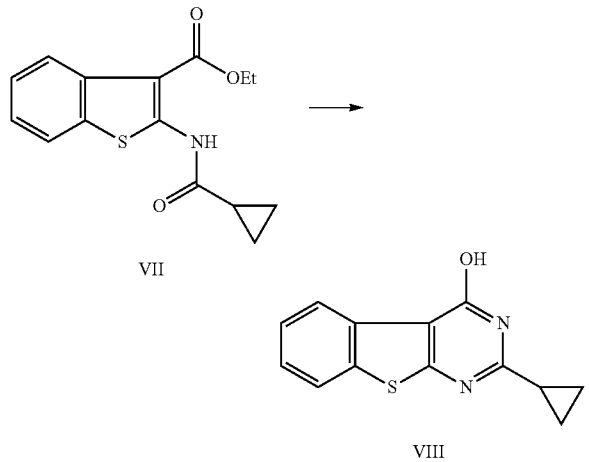

A suspension of 10 millimol VII in 10 milliliter 25% aqueous NH₃ was stirred at 90° C. for 24 hours in closed vial. The reaction mixture was cooled down to room temperature, and poured onto crushed ice with continuous stirring then collected by filtration. The product was washed with water and n-hexane, then dried.

Yield: 75%

Preparation of compounds 16-20

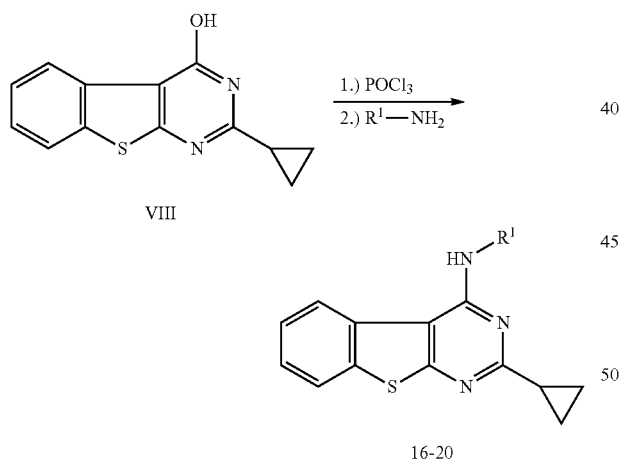

The solution of 1 millimol VIII in 5 milliliter POCl₃ was stirred at 100° C. for 3 hours. The reaction mixture was cooled down to room temperature, and poured onto crushed ice with continuous stirring. The solid was filtered off, washed with n-hexane and dried over P₂O₅. This product and 2 millimol amine reagent were solved in 2.5 milliliter propan-2-ol, and the solution was stirred at 100° C. for 6 hours in closed vial. The reaction mixture was poured onto crushed ice with continuous stirring, the pH was adjusted with 1N aqueous HCl to pH=7. The solid was filtered off, washed with water and n-hexane then dried.

Yields: 70-88%

EXAMPLE 4

Process for the Preparation of Compound 16-20

| Comp | A | R¹ | R² | |
|---|---|---|---|---|
| 16 | CH | 3-F—Ph | cPr | (2-Cyclopropyl-benzo[4,5]thieno[2,3-d]pyrimidin-4-yl)-(3-fluoro-phenyl)-amine |
| 17 | CH | 3-Cl—Ph | cPr | (2-Cyclopropyl-benzo[4,5]thieno[2,3-d]pyrimidin-4-yl)-(3-chloro-phenyl)-amine |
| 18 | CH | 3-Br—Ph | cPr | (2-Cyclopropyl-benzo[4,5]thieno[2,3-d]pyrimidin-4-yl)-(3-bromo-phenyl)-amine |
| 19 | CH | 3-OH—Ph | cPr | 3-(2-Cyclopropyl-benzo[4,5]thieno[2,3-d]pyrimidin-4-ylamino)-phenol |
| 20 | CH | 3-OMe—Ph | cPr | (2-Cyclopropyl-benzo[4,5]thieno[2,3-d]pyrimidin-4-yl)-(3-methoxy-phenyl)-amine |

Physicochemical Properties of Compounds 16-20

| Comp | MW [g/mol] | mp [° C.] | 1H-NMR δ [ppm] in DMSO-d₆ |
|---|---|---|---|
| 16 | 335.41 | 193 | 1.04(bs, 4H, CH2), 2.15(m, 1H, CH), 6.94(bs, 1H, ArH), 7.59(m, 5H, ArH), 8.10(d, 1H, ArH, J = 7.38), 8.47(d, 1H, ArH, J = 7.62), 9.21(s, 1H, NH) |
| 17 | 351.86 | 188 | 1.02(bs, 4H, CH2), 2.15(m, 1H, CH), 7.40(m, 6H, ArH), 7.87(s, 1H, ArH), 8.10(d, 1H, ArH, J = 6.23), 8.48(d, 1H, ArH, J = 5.53), 9.22(s, 1H, NH) |
| 18 | 396.31 | 180 | 1.02(bs, 4H, CH2), 2.15(m, 1H, CH), 7.31(m, 2H, ArH), 7.57(m, 2H, ArH), 7.71(d, 1H, ArH, J = 7.59), 8.01(s, 1H, ArH), 8.09(d, 1H, ArH, J = 7.59), 8.48(d, 1H, ArH, J = 7.56), 9.13(s, 1H, NH) |
| 19 | 333.41 | 222 | 1.04(bs, 4H, CH2), 2.14(m, 1H, CH), 7.16(m, 3H, ArH), 7.56(m, 3H, ArH), 8.10(d, 1H, ArH, J = 7.38), 8.45(d, 1H, ArH, J = 7.44), 9.04(s, 1H, NH) |
| 20 | 347.44 | 198 | 1.04(bs, 4H, CH2), 2.14(m, 1H, CH), 2.50(s, 3H, CH3), 6.72(m, 1H, ArH), 7.51(m, 5H, ArH), 8.09(d, 1H, ArH, J = 7.68), 8.46(d, 1H, ArH, J = 7.41), 9.02(s, 1H, NH) |

EXAMPLE 5

Preparation of 2-Amino-benzo[b]thiophene-3-carboxylic acid ethyl ester (IX)

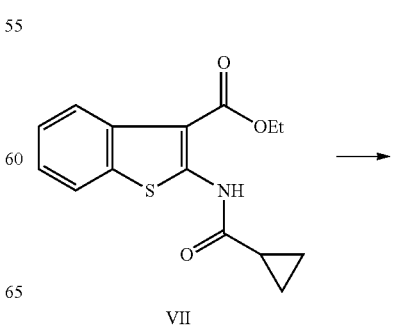

-continued

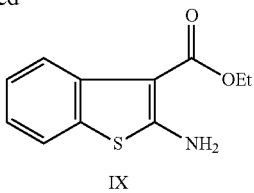

The solution of 10 millimol VII in 50 milliliter methanesulfonic acid was stirred at room temperature for 48 hours. The reaction mixture was poured onto icecold 25% aqueous NH₃ solution, the soliw was filtered off, washed with water and n-hexane, then dried.
Yield: 62%

Preparation of Benzo[4,5]thieno[2,3-d]pyrimidin-4-ol (X)

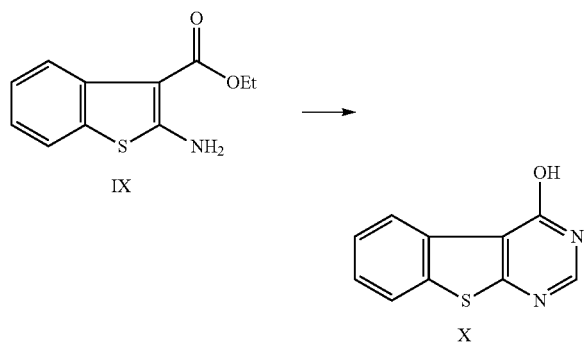

The solution of 10 millimol IX in 15 milliliter milliliter formamide was stirred at 100° C. for 3 hours then cooled down to room temperature. The reaction mixture was poured onto crushed ice with continuous stirring then collected by filtration. The product was washed with water and n-hexane, then dried.
Yield: 72%

EXAMPLE 5

Preparation of Compounds 21-23

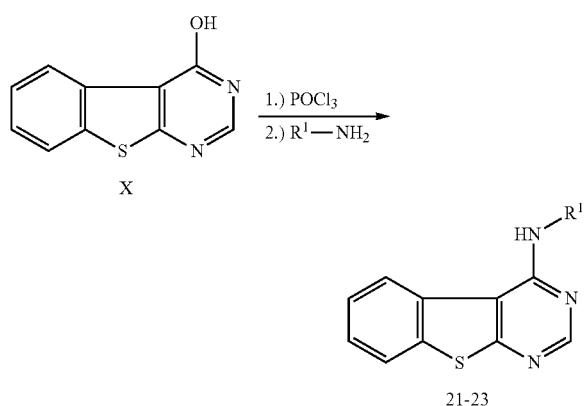

The solution of 1 millimol X in 5 milliliter POCl₃ was stirred at 100° C. for 3 hours. The reaction mixture was cooled down to room temperature, and poured onto crushed ice with continuous stirring. The solid was filtered off, washed with n-hexane and dried over $P_2O_5$. This product and 2 millimol amine reagent were solved in 2.5 milliliter propan-2-ol, and the solution was stirred at 100° C. for 6 hours in closed vial. The reaction mixture was poured onto crushed ice, the pH was adjusted with 1N aqueous HCl to pH=7. The solid was filtered off, washed with water and n-hexane then dried.

Yields: 70-88%

Compound 21-23 were prepared according to this method.

| Comp | A | R¹ | R² | |
|---|---|---|---|---|
| 21 | CH | 3-F—Ph | H | Benzo[4,5]thieno[2,3-d]pyrimidin-4-yl-(3-fluoro-phenyl)-amine |
| 22 | CH | 3-Cl—Ph | H | Benzo[4,5]thieno[2,3-d]pyrimidin-4-yl-(3-chloro-phenyl)-amine |
| 23 | CH | 3-Br—Ph | H | Benzo[4,5]thieno[2,3-d]pyrimidin-4-yl-(3-bromo-phenyl)-amine |

Physicochemical Properties of Compounds 21-23

| Comp | MW [g/mol] | mp [° C.] | ¹H-NMR δ [ppm] in DMSO-d₆ |
|---|---|---|---|
| 21 | 295.34 | 171 | 6.99(bs, 1H, ArH), 7.61(m, 5H, ArH), 8.15(bs, 1H, ArH), 8.55(d, 1H, ArH, J = 6.78), 8.64(s, 1H, ArH), 9.29(s, 1H, NH) |
| 22 | 311.80 | 168 | 7.20(d, 1H, ArH, J = 7.68), 7.42(t, 1H, ArH, J = 7.89), 7.66(m, 3H, ArH), 7.82(s, 1H, ArH), 8.16(d, 1H, ArH, J = 6.72), 8.56(d, 1H, ArH, J = 7.77), 8.63(s, 1H, ArH), 9.24(s, 1H, NH) |
| 23 | 356.25 | 160 | 7.62(bs, 2H, ArH), 7.36(bs, 2H, ArH), 8.16(d, 1H, ArH, J = 6.63), 7.95(s, 1H, ArH), 7.72(d, 1H, ArH, J = 6.57), 8.57(d, 1H, ArH, J = 7.53), 8.63(s, 1H, ArH), 9.22(s, 1H, NH) |

EXAMPLE 6

Biological Results

General description of the kinase assays: the kinase activity was assayed in 96-well microtiter plates at a final compound concentration of 10 μM in a total volume of 50 μl. Compounds were dissolved in 100% DMSO to prepare a 10 mM stock solution and than diluted with buffer to reach a 10 μM (or the required) final concentration. The kinase concentration was used to yield 10% ATP turn over. The ATP concentration was used at the $Km_{ATP}$ and 12.5 μCi/ml adenosine 5'[γ-33P]triphosphate. The substrate concentration was used at 5 fold excess over the $K_m$ for the substrate. The reaction was incubated for 1 hour at room temperature and stopped by addition of 10 μl 50 mM EDTA. The assay was transferred to a 96 well MAPH filter plate (Millipore). The radioactivity was counted on a Microbeta microplate counter.

Inhibitory activity of prepared compounds at 10 μM concentration (percent of inhibition):

|   | 1 | 2 | 3 | 4 | 5 | 6 | 7 | 8 | 9 | 10 | 11 | 12 |
|---|---|---|---|---|---|---|---|---|---|---|---|---|
| EGFR | 97 | 98 | 100 | 98 | 99 | 99 | 100 | 96 | 66 | 23 | 4 | 5 |
| AKT1/PKBa | −5 | −7 | −27 | 1 | −25 | −8 | −11 | 4 | −10 | 0 | 1 | −13 |
| Abl | 10 | −19 | −36 | −7 | −7 | 4 | −9 | 19 | −20 | −2 | 0 | −13 |
| CDK2/CycA | 3 | −1 | 4 | 16 | 9 | 11 | −1 | 12 | −10 | −11 | −5 | −8 |
| CK1-alpha | 6 | 6 | 17 | 5 | 7 | 7 | 5 | 4 | −3 | 4 | −1 | −3 |
| GSK-3beta | 7 | 3 | −10 | −2 | −6 | −1 | 2 | 8 | −6 | −8 | −3 | 0 |
| IKK-beta | 23 | 19 | 11 | 12 | 10 | 8 | 9 | 16 | −2 | 10 | 4 | 9 |
| InsR | −7 | −6 | −9 | −7 | −7 | 44 | −16 | 36 | 3 | 2 | −6 | 22 |
| Jnk1a1 | −4 | −3 | 4 | 6 | −3 | 15 | −7 | 20 | −6 | −12 | −3 | −5 |
| Kit | 13 | −5 | −2 | 2 | −5 | 7 | 10 | 20 | −6 | −12 | −1 | −8 |
| MAPK-ERK1 | −8 | −14 | 0 | 8 | −5 | 5 | −9 | 12 | 2 | 9 | 4 | 0 |
| PDGFR-beta | 4 | 4 | 1 | 0 | −5 | −12 | 15 | 6 | −2 | −5 | −4 | −11 |
| ROCK2 | 3 | 6 | 12 | 7 | −2 | 6 | 3 | −11 | 5 | 6 | 6 | 5 |
| RSK1 | −18 | −22 | 23 | 6 | 19 | 19 | −15 | 6 | 2 | −12 | −14 | 0 |
| SRPK1 | 11 | −5 | 8 | 6 | 7 | 9 | −3 | −4 | 7 | 18 | −5 | 21 |
| c-Raf | 23 | 16 | −4 | 14 | 0 | 12 | −20 | 11 | −6 | −3 | 2 | −3 |
| c-Src | 13 | 6 | 17 | 24 | 8 | 12 | 25 | 16 | 3 | 3 | 8 | 4 |
| cMet | 1 | −10 | −8 | 2 | −4 | 4 | −7 | 9 | −14 | 3 | 3 | −6 |
| P56Lck | 10 | 25 | 17 | 9 | −5 | 11 | 30 | 2 | 0 | 3 | −7 | 9 |
| P70S6K | −23 | −26 | 4 | 2 | 1 | −7 | −17 | 7 | 0 | 6 | 20 | 9 |

|   | 13 | 14 | 15 | 16 | 17 | 18 | 19 | 20 | 21 | 22 | 23 |
|---|---|---|---|---|---|---|---|---|---|---|---|
| EGFR | 26 | 72 | 9 | 60 | 86 | 87 | 54 | 46 | 98 | 98 | 99 |
| AKT1/PKBa | −2 | −1 | −9 | −7 | −1 | 0 | −5 | −2 | 3 | −7 | 9 |
| Abl | −15 | −3 | 12 | 3 | 7 | −2 | 3 | 7 | −4 | 8 | −10 |
| CDK2/CycA | −18 | −3 | −14 | −2 | −2 | −2 | −12 | 4 | −10 | −6 | 12 |
| CK1-alpha | 0 | 0 | 5 | 0 | 0 | 10 | 9 | 3 | 0 | −2 | 7 |
| GSK-3beta | −6 | 2 | −6 | 1 | 3 | 0 | 7 | 0 | 3 | 5 | −3 |
| IKK-beta | −9 | −6 | 12 | −4 | 8 | 3 | 12 | 9 | 2 | 11 | −5 |
| InsR | 9 | −3 | 23 | 2 | −5 | 5 | 11 | −12 | 7 | 18 | 4 |
| Jnk1a1 | −9 | −4 | −3 | −4 | −8 | −7 | −2 | −5 | −2 | 0 | −10 |
| Kit | −12 | −12 | 1 | −1 | 11 | 5 | 3 | 8 | −4 | 1 | 6 |
| MAPK-ERK1 | −6 | −4 | 6 | 6 | 2 | −6 | 2 | 21 | 1 | 5 | 8 |
| PDGFR-beta | −14 | −4 | −7 | −3 | 0 | 0 | −1 | −1 | −3 | −8 | 10 |
| ROCK2 | 3 | 12 | 9 | 9 | 2 | 4 | 7 | 0 | 4 | 4 | 2 |
| RSK1 | −18 | −4 | 8 | 2 | −7 | −4 | −11 | 7 | 1 | −2 | −4 |
| SRPK1 | 11 | 11 | 12 | 10 | 9 | 12 | 3 | 18 | 8 | 6 | 6 |
| c-Raf | −7 | −5 | −13 | −4 | 12 | −8 | −4 | 9 | −2 | −6 | 3 |
| c-Src | 1 | 5 | 5 | 2 | 1 | 22 | 11 | 23 | 3 | 9 | 7 |
| cMet | −4 | −7 | −6 | 0 | −5 | −7 | −12 | −2 | 1 | 5 | 4 |
| P56Lck | 12 | 6 | −5 | 7 | 9 | 11 | 3 | 0 | −9 | 11 | 4 |
| P70S6K | 9 | 2 | 4 | 8 | 7 | 2 | 3 | 9 | 7 | 5 | −1 |

Ten compounds were found to inhibit EGFR-PTK with higher than 96% inhibitory activity at 10 µM concentration. Most active compounds were tested on EGFR-PTK assay to determine their $IC_{50}$ values.

| Compound | EGFR $IC_{50}$, nM |
|---|---|
| 2 | 12.36 |
| 3 | 2.61 |
| 4 | 16.78 |
| 6 | 10.52 |
| 7 | 12.81 |
| 21 | 26.92 |
| 23 | 8.08 |

The invention claimed is:

1. A compound of the formula (I) or pharmaceutically acceptable salt thereof:

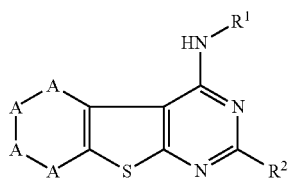

(I)

wherein:

A is methylene ($CH_2$) or methylidene (CH), $R^1$: monosubstituted phenyl, wherein a substituent is selected from the group of consisting of fluoro, chloro, bromo, trifluoromethyl, $NH_2$, CN, methoxy, nitro, and OH, $R^2$: hydrogen, alkyl or cycloalkyl, with the proviso that $R^2$ is not hydrogen when the phenyl substituent of $R^1$ is 3- or 4-trifluoromethyl, 3- or 4-fluoro, 4-chloro, 4-bromo or 4-methoxy, and A is methylene.

2. The compound or pharmaceutically acceptable salt thereof according to claim 1 selected from the group consisting of:

(2-fluoro-phenyl)-(5,6,7,8-tetrahydro-benzo[4,5]thieno [2,3-d]pyrimidin-4-yl)-amine;

(3-bromo-phenyl)-(5,6,7,8-tetrahydro-benzo[4,5]thieno [2,3-d]pyrimidin-4-yl)-amine;

N-(5,6,7,8-tetrahydro-benzo[4,5]thieno[2,3-d]pyrimidin-4-yl)-benzene-1,3-diamine;

3-(5,6,7,8-tetrahydro-benzo[4,5]thieno[2,3-d]pyrimidin-4-ylamino)-benzonitrile;

(4-chloro-phenyl)-(5,6,7,8-tetrahydro-benzo[4,5]thieno [2,3-d]pyrimidin-4-yl)-amine;

N-(5,6,7,8-Tetrahydro-benzo[4,5]thieno[2,3-d]pyrimidin-4-yl)-benzene-1,4-diamine;

(3-chloro-phenyl)-(2-cyclopropyl-5,6,7,8-tetrahydro-benzo[4,5]thieno[2,3-d]pyrimidin-4-yl)-amine;

3-(2cyclopropyl-5,6,7,8-tetrahydro-benzo[4,5]thieno[2,3-d]pyrimidin-4-ylamino)-phenol;
(2-cyclopropyl-5,6,7,8-tetrahydro-benzo[4,5]thieno[2,3-d]pyrimidin-4-yl)-(3-trifluoromethyl-phenyl)-amine;
N-(2-cyclopropyl-5,6,7,8-tetrahydro-benzo[4,5]thieno[2,3-d]pyrimidin-4-yl)-benzene-1,3-diamine;
(2-cyclopropyl-5,6,7,8-tetrahydro-benzo[4,5]thieno[2,3-d]pyrimidin-4-yl)-(3-nitro-phenyl)-amine;
3-(2-cyclopropyl-5,6,7,8-tetrahydro-benzo[4,5]thieno[2,3-d]pyrimidin-4-ylamino)-benzonitrile;
(2-cyclopropyl-5,6,7,8-tetrahydro-benzo[4,5]thieno[2,3-d]pyrimidin-4-yl)-(3-methoxy-phenyl)-amine;
(2-cyclopropyl-benzo[4,5]thieno[2,3-d]pyrimidin-4-yl)-(3-fluoro-phenyl)-amine;
(2-cyclopropyl-benzo[4,5]thieno[2,3-d]pyrimidin-4-yl)-(3-chloro-phenyl)-amine;
(2-cyclopropyl-benzo[4,5]thieno[2,3-d]pyrimidin-4-yl)-(3-bromo-phenyl)-amine;
3-(2-cyclopropyl-benzo[4,5]thieno[2,3-d]pyrimidin-4-ylamino)-phenol;
(2-cyclopropyl-benzo[4,5]thieno[2,3-d]pyrimidin-4-yl)-(3-methoxy-phenyl)-amine;
benzo[4,5]thieno[2,3-d]pyrimidin-4-yl-(3-fluoro-phenyl)-amine;
benzo[4,5]thieno[2,3-d]pyrimidin-4-yl-(3-chloro-phenyl)-amine;
benzo[4,5]thieno[2,3-d]pyrimidin-4-yl-(3-bromo-phenyl)-amine;
and pharmaceutically acceptable salts thereof.

3. A method of treatment of proliferative diseases related to EGFR activity, said method comprising administering to a patient the compound or pharmaceutical acceptable salt thereof according to claim 1.

4. The method according to claim 3 wherein the compound or pharmaceutically acceptable salt thereof is selected from the group consisting of:
(2-fluoro-phenyl)-(5,6,7,8-tetrahydro-benzo[4,5]thieno[2,3-d]pyrimidin-4-yl)-amine;
(3-bromo-phenyl)-(5,6,7,8-tetrahydro-benzo[4,5]thieno[2,3-d]pyrimidin-4-yl)-amine;
N-(5,6,7,8-tetrahydro-benzo[4,5]thieno[2,3-d]pyrimidin-4-yl)-benzene-1,3-diamine;
3-(5,6,7,8-tetrahydro-benzo 4,5]thieno[2,3-d]pyrimidin-4-ylamino)-benzonitrile;
(4-chloro-phenyl)-(5,6,7,8-tetrahydro-benzo[2,3-d]pyrimidin-4-yl)-amine;
N-(5,6,7,8-Tetrahydro-benzo[4,5]thieno[2,3-d]pyrimidin-4-yl)-benzene-1,4-diamine;
(3-chloro-phenyl)-(2-cyclopropyl-5,6,7,8-tetrahydro-benzo[4,5]thieno[2,3-d]pyrimidin-4-yl)-amine;
3-(2cyclopropyl-5,6,7,8-tetrahydro-benzo[4,5]thieno[2,3-d]pyrimidin-4-ylamino)-phenol;
(2-cyclopropyl-5,6,7,8-tetrahydro-benzo[4,5]thieno[2,3-d]pyrimidin-4-yl)-(3-trifluoromethyl-phenyl)-amine;
N-(2-cyclopropyl-5,6,7,8-tetrahydro-benzo[4,5]thieno[2,3-d]pyrimidin-4-yl)-benzene-1,3-diamine;
(2-cyclopropyl-5,6,7,8-tetrahydro-benzo[4,5]thieno[2,3-d]pyrimidin-4-yl)-(3-nitro-phenyl)-amine;
3-(2-cyclopropyl-5,6,7,8-tetrahydro-benzo[4,5]thieno[2,3-d]pyrimidin-4-ylamino)-benzonitrile;
(2-cyclopropyl-5,6,7,8-tetrahydro-benzo[4,5]thieno[2,3-d]pyrimidin-4-yl)-(3-methoxy-phenyl)-amine;
(2-cyclopropyl-benzo[4,5]thieno[2,3-d]pyrimidin-4-yl)-(3-fluoro-phenyl)-amine;
(2-cyclopropyl-benzo[4,5]thieno[2,3-d]pyrimidin-4-yl)-(3-chloro-phenyl)-amine;
(2-cyclopropyl-benzo[4,5]thieno[2,3-d]pyrimidin-4-yl)-(3-bromo-phenyl)-amine;
3-(2-cyclopropyl-benzo[4,5]thieno[2,3-d]pyrimidin-4-ylamino)-phenol;
(2-cyclopropyl-benzo[4,5]thieno[2,3-d]pyrimidin-4-yl)-(3-methoxy-phenyl)-amine;
benzo[4,5]thieno[2,3-d]pyrimidin-4-yl-(3-fluoro-phenyl)-amine;
benzo[4,5]thieno[2,3-d]pyrimidin-4-yl-(3-chloro-phenyl)-amine;
benzo[4,5]thieno[2,3-d]pyrimidin-4-yl-(3-bromo-phenyl)-amine.

5. A method of reducing EGFR expression in a patient, said method comprising administering to the patient the compound or pharmaceutical acceptable salt thereof according to claim 1.

* * * * *